United States Patent
Okamoto et al.

(10) Patent No.: US 8,710,231 B2
(45) Date of Patent: Apr. 29, 2014

(54) INHIBITOR OF CASEIN KINASE 1DELTA AND CASEIN KINASE 1E

(75) Inventors: Masako Okamoto, Tokyo (JP); Kiyoshi Takayama, Sapporo (JP)

(73) Assignees: Pharmadesign, Inc., Tokyo (JP); NB Health Laboratory Co., Ltd., Sapporo-shi (JP)

( * ) Notice: Subject to any disclaimer, the term of this patent is extended or adjusted under 35 U.S.C. 154(b) by 0 days.

(21) Appl. No.: 13/816,180

(22) PCT Filed: Aug. 8, 2011

(86) PCT No.: PCT/JP2011/068034
§ 371 (c)(1),
(2), (4) Date: Feb. 8, 2013

(87) PCT Pub. No.: WO2012/020726
PCT Pub. Date: Feb. 16, 2012

(65) Prior Publication Data
US 2013/0137730 A1   May 30, 2013

(30) Foreign Application Priority Data
Aug. 9, 2010 (JP) .................................. 2010-178549

(51) Int. Cl.
| C07D 413/00 | (2006.01) |
| C07D 419/00 | (2006.01) |
| C07D 409/00 | (2006.01) |
| C07D 411/00 | (2006.01) |
| A61K 31/44  | (2006.01) |
| A01N 43/40  | (2006.01) |

(52) U.S. Cl.
USPC .................. 546/271.4; 546/268.4; 546/279.7; 546/280.4; 514/340; 514/336; 514/342

(58) Field of Classification Search
USPC ........................................ 514/340; 546/271.4
See application file for complete search history.

(56) References Cited

U.S. PATENT DOCUMENTS 7,531,539 B2 *   5/2009   Fink et al. ..................... 514/243

FOREIGN PATENT DOCUMENTS

| JP | 2003-505453 A | 2/2003 |
| JP | 2004-530643 A | 10/2004 |
| JP | 2008-510704 A | 4/2008 |
| JP | 2008-510712 A | 4/2008 |
| WO | 2009/037394 A2 | 3/2009 |
| WO | 2010/092660 A1 | 8/2010 |

OTHER PUBLICATIONS

Masako Okamoto, Kiyoshi Takayama, Tomoko Shimizu, Ayumu Muroya, Toshio Furuy; Bioorganic & Medicinal Chemistry 18 (2010) 2728-2734.*

Wermuth, Camille Georges; Practice of Medicinal Chemistry (2008, 3rd Edition). Elsevier. pp. 293, 424, 448 and 451.*

Knippschild, Uwe et al., "The casein kinase 1 family; participation in multiple cellular processes in eukaryotes", Cellular Signalling, No. 17, p. 675-689 (2005).

Ebisawa, Takashi, "Circadian Rhythms in the CNS and Peripheral Clock Disorders: Human Sleep Disorders and Clock Genes", Journal of Pharmacological Sciences, vol. 103, p. 150-154, (2007).

Ko, Caroline H. et al., "Molecular components of the mammalian circadian clock", Human Molecular Genetics, vol. 15, No. 2, p. R271-R277 (2006).

Badura, Lori et al., "An Inhibitor of Casein Kinase Iε Induces Phase Delays in Circadian Rhythms under Free-Running and Entrained Conditions", The Journal of Pharmacology and Experimental Therapeutics, vol. 322, No. 2, p. 730-738 (2007).

Xu, Y. et al., "Modeling of a human circadian mutation yields novel insights into clock regulation by PER2", NIH Public Access, Cell, Jan. 12, vol. 128, No. 1, p. 59-70 (2007).

Li, Guibin et al., "Casein Kinase 1 Delta Phosphorylates Tau and Disrupts Its Binding to Microtubules"; The Journal of Biological Chemistry, vol. 279, No. 16, p. 15938-15945, Apr. 16, 2004.

(Continued)

*Primary Examiner* — John Mabry
*Assistant Examiner* — Daniel Carcanague
(74) *Attorney, Agent, or Firm* — Westerman, Hattori, Daniels & Adrian, LLP

(57) ABSTRACT

There is provided a novel oxazolone derivative having inhibitory activity against casein kinase 1δ and casein kinase 1ε. In addition, the present inhibitor inhibits casein kinase 1δ and casein kinase 1ε, and thus there is also provided a pharmaceutical agent useful for the treatment and/or prevention of diseases, with the pathological conditions of which the activation mechanism of casein kinase 1δ or casein kinase 1ε is associated. There is further provided a pharmaceutical agent useful for the treatment of, particularly, circadian rhythm disorder (including sleep disorder), central neurodegenerative disease, and cancer. An inhibitor of casein kinase 1δ and casein kinase 1ε comprising, as an active ingredient, an oxazolone derivative represented by the following general formula (1), a salt thereof, a solvate thereof, or a hydrate thereof:

[Formula 1]

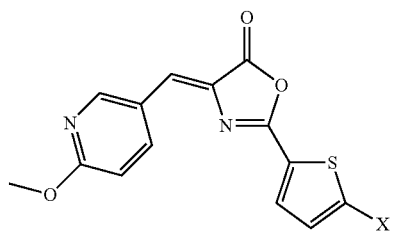

(1)

wherein X represents a halogen atom which is fluorine, chlorine, bromine or iodine.

2 Claims, No Drawings

(56) References Cited

OTHER PUBLICATIONS

Hanger, Diane P. et al., "Novel Phosphorylation Sites in Tau from Alzheimer Brain Support a Role for Casein Kinase 1 in Disease Pathogenesis", The Journal of Biological Chemistry, vol. 282, No. 32, p. 23645-23654, Aug. 10, 2007.

Flajolet, Marc et al., "Regulation of Alzheimer's disease amyloid-β formation by casein kinase I", Proc National Academy of Sciences (PNAS), vol. 104, No. 10, p. 4159-4164, Mar. 6, 2007.

Brockschmidt, C. et al., "Anti-apoptotic and growth-stimulatory functions of CK1 delta and epsilon in ductal adenocarcinoma of the pancreas are inhibited by IC261 in vitro and in vivo", GUT Online, No. 57, p. 799-806, Jan. 18, 2008.

Mashhoon, Neda et al., "Crystal Structure of a Conformation-selective Casein Kinase-1 Inhibitor", The Journal of Biological Chemistry, vol. 275, No. 26, p. 20052-20060, Jun. 30, 2000.

Rena, Graham et al., "D4476, a cell-permeant inhibitor of CK1, suppresses the site-specific phosphorylation and nuclear exclusion of FOXO1a", European Molecular Biology Organization, EMBO reports, vol. 5, No. 1, p. 60-65 (2004).

Godl, Klaus et al., "An efficient proteomics method to identify the cellular targets of protein kinase inhibitors", Proc. National Academy of Sciences (PNAS), vol. 100, No. 26, p. 15434-15439, Dec. 23, 2003.

Cozza, G. et al., "Identification of novel protein kinase CK1 delta (CK1delta) inhibitors through structure-based virtual screening", Bioorg Med Chem Lett., vol. 18, No. 20, p. 5672-5675. Oct. 15, 2008 (17 pages).

Longenecker, K.L et al., 1CKI.txt, pp. 1-456, Aug. 25, 1995.
Longenecker, K.L et al., 1CKJ.txt, pp. 1-380, Aug. 25, 1995.
2C47.txt, pp. 1-609, May 15, 2006.
2CHL.txt, pp. 1-609, May 15, 2006.
2CMW.txt, pp. 1-609, May 15, 2006.
2IZR.txt, pp. 1-1582, Jul. 26, 2006.
2IZS.txt, pp. 1-470, Mar. 15, 2006.
2IZT.txt, pp. 1-470, Mar. 15, 2006.
2IZU.txt, pp. 1-505, Jul. 26, 2006.
International Search Report of PCT/JP2011/068034, date of mailing date Sep. 6, 2011.

* cited by examiner

INHIBITOR OF CASEIN KINASE 1DELTA AND CASEIN KINASE 1E

TECHNICAL FIELD

The present invention relates to an inhibitor of casein kinase 1δ and casein kinase 1ε, which comprises, as an active ingredient, an oxazolone derivative, a salt thereof, a solvate thereof, or a hydrate thereof. The present invention relates to a pharmaceutical agent for treating diseases, with the pathological conditions of which the activation of casein kinase 1δ or casein kinase 1ε is associated. The present invention relates to a pharmaceutical agent comprising the inhibitor of casein kinase 1δ and casein kinase 1ε, which is useful for the treatment and/or prevention or, particularly, circadian rhythm disorder (including sleep disorder), central neurodegenerative disease, and cancer, among the diseases, with the pathological conditions of which the activation of casein kinase 1δ or casein kinase 1ε is associated.

BACKGROUND ART

Casein kinase 1 belongs to serine/threonine kinase (which phosphorylates a tyrosine residue in some cases). As its isoforms in mammals seven types of isoforms, namely, α, β, γ1, γ2, γ3, δ, and ε, have been known. It has been known that these isoforms phosphorylate various types of different substrate proteins, and that the isoforms are able to activate, inactivate, stabilize or destabilize the functions of the proteins, and thus they are associated with regulation of the functions of various types of different organisms. Mammalian casein kinase 1δ or casein kinase 1ε has, as a structure thereof, a kinase domain that is similar to those of other isoforms. However, the N-terminal and C-terminal domains thereof are different from those of other isoforms. That is to say, the C-terminal domain has a plurality of autophosphorylation sites, and it is considered to be involved in regulation of autoenzyme activity. In addition, such a kinase domain comprises a sequence assumed to be associated with nuclear translocation (NLS: nuclear location signal) and a kinesin-like domain (KHD: kinesin homology domain).

It has been known that casein kinase 1δ and casein kinase 1ε are associated with circadian rhythm disorder, that casein kinase 1δ and casein kinase 1ε, are associated with central neurodegenerative disease, and that casein kinase 1δ and casein kinase 1ε are associated with cancer. Detailed information regarding the association of these casein kinases with the pathological conditions of the above-mentioned diseases has being known in studies regarding the interaction between the casein kinase 1δ and casein kinase 1ε, and target proteins interacting with the casein kinase 1δ and casein kinase 1ε, such as substrate proteins interacting with the corresponding casein kinase 1δ and casein kinase 1ε. Specific examples of a substrate protein phosphorylated by the Casein kinase 1δ and casein kinase 1ε include a period protein (Per), a tan protein (tau), p53, and β-catenin.

Today, the core of the biological clock acting as a central generator of the circadian rhythm is considered to consist of approximately 10 types of gene interaction networks called "clock genes." Among these 10 types of gene groups, Per 1, 2 and 3 (Period 1, 2 and 3), Cry 1 and 2 (cryptochrome 1 and 2), Bmal1 (brain and muscle ARNT-like 1), and Clock (circadian locomotor output cycles kaput) encode transcription factors. On the other hand, CK1δ and 1ε encode casein kinase 1δ and casein kinase 1ε that phosphorylate these transcription factors. It has been known that the functional abnormality of these clock genes has influence on the circadian rhythm phenotypes of various types of animals including humans. Since the molecular mechanism of such a biological clock is well conserved beyond species, it is advantageous in that the studies of clock genes can be carried out in in vitro tests regarding the abnormality of the circadian rhythm phenotypes of humans. The Clock governs a pathway for generating activation signals, among biological clock interaction networks, and activates Per, Cry and other downstream target genes. On the other hand, Per and Cry, which govern a pathway for generating regulatory signals, act to suppress the activity of the Clock. Casein kinase 1δ and casein kinase 1ε phosphorylate Per and Cry, so as to promote the cytoplasmic degradation of Per. Moreover, the results of such phosphorylation are associated with the control of the nuclear translocation of these transcription factors and the stability thereof in the nucleus. Thus, it has been considered that the rhythm of internal molecular vibrations is governed in a living body. In the case of mammals, the biological clock is present in the suprachiasmatic nucleus (SCN), and this SCM biological clock operates together with the gene expression biological clocks of central and peripheral tissues, other than SCN.

Per has been known as a circadian rhythm regulatory protein in a living body. The mRNA and protein levels of Per vibrate in response to the circadian rhythm, and are closely associated with the control of the biological clock. For instance, it has been known that, with a decrease in the phosphorylation caused by casein kinase 1ε or casein kinase 1δ, a genetic disease having a human Per2 phosphorylation site mutation (S662G) progresses to familial advanced sleep phase syndrome (FASPS). This shows that Per plays an important role in sleep regulation. It has been known that a change in the intracellular protein amount of Per is controlled by the phosphorylation caused by casein kinase 1ε or casein kinase 1δ. That is, it has been known that, if Per is phosphorylated by these kinases, the stability of the protein significantly decreases.

Xu, Y. et al. have reported that human Per2 phosphorylation site mutated (S662G) transgenic mice were found to have the same phenotype as FASPS found in humans. Moreover, these researchers have studied the influence caused by a change in the expression level of casein kinase 1δ using hybrid mice between the above-described transgenic mice and casein kinase 1δ WT mice (WT: wild type) or casein kinase 1δ+/−(heterozygous knockout) mice. As a result, the researchers have reported that the above-described phenotype has been influenced thereby, and that the abnormality of the circadian rhythm phenotype found in the wild-type mice was corrected in the +/− mice. This report describes the phosphorylation status of Per2 and the importance of the association of casein kinase 1δ with the phosphorylation (Non Patent Literature 5). Furthermore, Badula, Loi et al. have reported that the phase of circadian rhythm can be significantly delayed by subcutaneously administering to rats a casein kinase 1ε inhibitory compound, 4-[3-cyclohexyl-5-(4-fluorophenyl)-3H-imidazol-4-yl]-pyrimidin-2-ylamine (PF-670462) (Non Patent Literature 4). Thus, the phosphorylation status of Per has a relationship with circadian rhythm, and the inhibitor of casein kinase 1δ or casein kinase 1ε provides a novel method of adjusting such circadian rhythm. It can be anticipated that a technique of shilling or resetting the phase of circadian rhythm contributes to the treatment of circadian rhythm disorder including various types of sleep disorders.

However, conventional inhibitors including PP-670462 as a typical example exhibit inhibitory action even against kinases (e.g. p38α) that cause concerns about the expression of side effects. Thus, such conventional inhibitors have not yet been completed as pharmaceutical products.

Almost no pharmaceutical agents for directly treating circadian rhythm disorder have been known in prior art techniques. In addition, as therapeutic agents for such sleep disorders, sleep inducing drugs have been developed and used in clinical sites. On the other hand, the development of drugs for improving circadian rhythm sleep disorder (shift work sleep disorder, jet lag syndrome, advanced sleep phase syndrome, and delayed sleep phase syndrome) and the like has not yet been completed. Also, drug therapy, which is based on the technique of shifting or resetting the phase of circadian rhythm for other sleep disorders (insomnia, sleep-related breathing disorder, central hypersomnia, parasomnia, and sleep-related movement disorder), has not yet been completed.

Hereinafter, the correlation of casein kinase 1δ or casein kinase 1ε with central neurodegenerative disease, and in particular, with Alzheimer's disease, will be described.

It has been well known that aggregation of a tau protein in an Alzheimer's disease lesion site is an important marker for the pathological conditions. Also, it has been well known that excessive phosphorylation of this tau protein is deeply associated with aggregation. A casein kinase 1 family that is excessively expressed in the lesion site is considered to include candidate kinases for phosphorylating the tau protein. Thus, among these casein kinases, Li, Guibon et al. have studied casein kinase 1δ using a HEK-293 cell expression line. As a result, they have demonstrated using a nonselective casein kinase 1 inhibitory compound, 3-[(2,3,6-trimethoxyphenyl)methylidenyl]-idolin-2-one (IC261), that casein kinase 1δ first associates with a tau protein in situ and the casein kinase 1δ directly phosphorylates the tau protein, and that the phosphorylated level in the site of the tan protein that is the same as that phosphorylated in vitro is increased due to the excessive expression of the casein kinase 1δ (Non Patent Literature 6). On the other hand, Hanger, Diane P. et al. have made a comparison by mass spectrometry between, what is called, insoluble tau (PHF-tau (paired helical filaments-tau)), which is an extremely phosphorylated aggregate obtained from the lesion site of an Alzheimer's disease patient, and the phosphorylation site of a healthy human, and have then identified a phosphorylation site characteristic for the lesion site of the Alzheimer's disease patient. At the same time, based on the characteristics of the phosphorylation site, they suggested that, as candidate kinases, casein kinase 1δ as well as glycogen synthase kinase 3β, is highly likely to be associated with the process of lesion development (Non Patent Literature 7).

Hereinafter, the correlation of casein kinase 1δ or casein kinase 1ε with central neurodegenerative disease, and particularly with Alzheimer's disease, will be further described.

With regard Alzheimer's disease, it has been considered that accumulation of amyloid-β (Aβ) showing toxic to nerve cells is associated with the lesion thereof. At the same time, it has been known that the expression of casein kinase 1 is increased in the lesion site of an Alzheimer's disease patient. It is considered that Aβ is formed by cleaving APP (amyloid precursor protein) with β-secretase (aspartyl protease β-secretase) and γ-secretase (presenin-dependent protease γ-secretase). Flajolet, Marc et al. have performed an in silico analysis to study a site commonly phosphorylated by casein kinases 1 that are assumed to be present in the sequences of the subunits of these APP, β-secretase and γ-secretase. Subsequently, based on the obtained results, they have attempted to excessively express casein kinase 1ε constitutively active to N2A cells (N2A-APP695 cells) that stably express APP. As a result, they have reported that the amounts of Aβ40 and Aβ42 had become approximately 2 times and 2.5 times higher than that of a control, respectively. Furthermore, they have also reported that, when a nonselective casein kinase 1 inhibitory compound IC261 was added to this system, the amounts of Aβ40 and Aβ42 were decreased, and further that the same results could be obtained also using other two different types of nonselective casein kinase 1 inhibitory compounds, CKI-7 and D4476 (Non Patent Literature 8).

These reports (Non Patent Literature 6, 7 and 8) strongly suggest that casein kinase 1, and particularly, casein kinase 1δ or casein kinase 1ε is associated with the development of Alzheimer's disease, and that Alzheimer's disease can be treated by inhibiting the activity of the above-described enzyme.

Moreover, the chromosome 21, in which an Alzheimer's disease-causing gene is assumed to be present, becomes trisomic (triploid) in the somatic cells of a Down's syndrome patient. Thus, it has been thought that Down's syndrome can be as model for the studies of the genetic background or development of Alzheimer's disease. In particular, abnormal accumulation of specific proteins, found in the two types of diseases, has been considered to be one important, pathological and biochemical indicator associated with the pathogenic mechanism thereof, and thus has been studied. As a matter of fact, it has been known that Down's syndrome patients often have Alzheimer's disease-like cerebral lesion after middle age (approximately 35 years old). These facts strongly suggest that, even regarding neurodegenerative disease associated with Down's syndrome, this disease can be treated by inhibiting the enzyme activity of casein kinase 1, and particularly, casein kinase 1δ or casein kinase 1ε.

In prior art techniques, there have been known almost no pharmaceutical agents for treating central neurodegenerative diseases including Alzheimer's disease, which involve, as a point of action, direct inhibition of the aggregation of a tau protein or amyloid β. In addition, in prior art techniques, drug therapy for impeding the progression of central neurodegenerative diseases based on the concerned mechanism has not yet been completed.

Hereinafter, the correlation of casein kinase 1δ or casein kinase 1ε with cancer, and particularly, with pancreatic cancer, will be described.

The casein kinase 1 family is associated with regulation of various important physiological activities in cells. The casein kinase 1 family phosphorylates a wide variety of substrate proteins. For example, a tumor suppressor factor p53 and an oncogene mdm2 are both important proteins for controlling canceration and, at the same time, are substrates of casein kinase 1. Depending on the phosphorylation status thereof, cell canceration is considered to be accelerated. Among isoforms of casein kinase 1, phosphorylation of p53 by casein kinase 1ε or casein kinase 1δ, a consequent change in the interaction between p53 and mdm2, and stabilization and activation of p53 have attracted a lot of attention. Furthermore, it has also been known that casein kinase 1ε or casein kinase 1δ is involved in a regulatory protein associated with the formation of a spindle as a central body during cell division, and that the casein kinase 1ε or casein kinase 1δ is involved in apoptosis by TRAIL (tumor necrosis factor-related apoptosis inducing factor) and Fas.

By the way, pancreatic ductal adenocarcinomas (PDACs) have been considered to be refractory cancers. Brockschmidt, C. et al. have studied that casein kinase 1ε or casein kinase 1δ is highly expressed in PDACs. Based on the obtained results, a nonselective casein kinase 1 inhibitory compound IC261 was added to a human pancreatic cancer cell line in vitro. As a result, suppression of the cell growth was observed. At the same time, the same pancreatic cancer cell line was transplanted into the subcutis of a mouse, and the nonselective casein kinase 1 inhibitory compound IC261 was then administered to the mouse. As a result, Brockschmidt, C. et al. have reported that a significant effect of suppressing the growth of tumor cells was obtained as in the case of a gemcitabine administration group (Non Patent Literature 9).

In prior art techniques, a pharmaceutical agent that can be used as an anticancer agent based on inhibition of casein kinase 1ε or casein kinase 1δ has not been known in the prior art. Moreover, in prior art techniques, drug therapy for treating refractory pancreatic cancer based on the concerned mechanism has not yet been completed.

CITATION LIST

Patent Literature

[Patent Literature 1] JP Patent Publication (Kohyo) No. 2008-510712 A
[Patent Literature 2] JP Patent Publication (Kohyo) No. 2008-510704 A Non Patent Literature

[Non Patent Literature 1] Uwe Knippschild et al., Cellular Signaling, 17, 675-689 (2005)
[Non Patent Literature 2] Takashi Ebisawa, J. Pharmacol. Sci., 103, 150-154 (2007)
[Non Patent Literature 3] Caroline H. Ko et Jpseph S. Takahashi, Hu. Mol. Genetics, 15(2) R271-R277 (2006)
[Non Patent Literature 4] Lori Badura et al, J. Pharmacol. Exp. Therapy, 322, 730-738 (2007)
[Non Patent Literature 5] Xu, Y. et al., Cell 128, 59-70 (2007)
[Non Patent Literature 6] Li, Guibin et al., J. Biol. Chem., 279(16), 15938-15945 (2004)
[Non Patent Literature 7] Hanger, Diane P. et al., J. Biol. Chem., 282(32) 23645-23654 (2007)
[Non Patent Literature 8] Flajolet, Marc et al., Proc. Nat. Acad. Sci., 104(10), 4159-4164 (2007)
[Non Patent Literature 9] Brockscbmidt, C. et al.: Gut, 57, 799-809 (2008)
[Non Patent Literature 10] Mashhoon, Neda et al., J. Biol. Chem., 275(26), 20052-20060 (2000)
[Non Patent Literature 11] Rena, Graham, et al., EMBO Rep., 5(1), 60-65, (2004)
[Non Patent Literature 12] Godl, Klaus, et al., Proc. Nat. Acad. Sci., 100(26), 15434-15439 (2003)
[Non Patent Literature 13] Cozza, Giorgio et al., Bioorg, Medicinal Chem. Lett, 18(20), 5622-5675 (2008)
[Non Patent Literature 14] Protein Data Bank [online], <URL:http://www.resb.org/pdh/>, ID No.: 2CMW (CK1gamma1), 2C47 (CK1gamma2), 2CHL, 2IZR, 2IZS, 2IZT, 2IZU (CK1gamma3), 1CKI, 1CKJ, (CK1delta)

DISCLOSURE OF INVENTION

Technical Problem

It is an object of the present invention to provide an inhibitor of casein kinase 1δ and casein kinase 1ε, which comprises, as an active ingredient, an oxazolone derivative, a salt thereof, a solvate thereof, or a hydrate thereof.

In addition, it is another object of the present invention to provide a pharmaceutical agent, which comprises the casein kinase 1δ and casein kinase 1ε selective inhibitor of the present invention as a pharmaceutically active ingredient, wherein the pharmaceutical agent is useful for the treatment and/or prevention of diseases, with the pathological conditions of which the activation of casein kinase 1δ or casein kinase 1ε is associated, whereby the functions of the casein kinase 1δ or casein kinase 1ε are regulated in vivo. Moreover, it is another object of the present invention to provide a pharmaceutical agent useful for the treatment and/or prevention of circadian rhythm disorder (including sleep disorder), central neurodegenerative disease and cancer, among the diseases, with the pathological conditions of which the activation of casein kinase 1δ or casein kinase 1ε is associated. Furthermore, it is another object of the present invention to provide a method for treating and/or preventing circadian rhythm disorder (including sleep disorder), central neurodegenerative disease and cancer, administering the above-described pharmaceutical agent to a subject.

Further, it is another object of the present invention to provide a novel oxazolone derivative, a pharmaceutically acceptable salt thereof, and a hydrate thereof.

Solution to Problem

To date, several compounds have been known as research reagents having casein kinase 1 inhibitory action, which are non-specific to casein kinase 1 isoforms. Representative examples of such a compound include IC261, D4476, and SB203580 (Non Patent Literature 10, 11 and 12). These compounds have not yet obtained properties sufficient to solve the problems. In the beginning, these compounds were anticipated to simply have casein kinase 1 selective inhibitory action, and they targeted casein kinase 1δ as an isoform. On the other hand, PF-670462 is a compound obtained as a result of requirements for achieving casein kinase 1ε selective inhibitory action. However, this compound also has inhibitory action against other kinases. It as incidentally found that this compound also has inhibitory action against casein kinase 1δ, and that the possession of this inhibitory action is pharmacologically significant (Non Patent Literature 4). Likewise, there have been known other compounds having such casein kinase 1ε selective inhibitory action, but their selective inhibition of isoforms is not clearly described (Patent Literatures 1 and 2). Moreover, it has been reported that a model was constructed on the basis of the information regarding the three-dimensional structure of a target protein, and that, what is called, virtual screening was then performed. However, the action of the obtained compound is just limited to inhibitory action against casein kinase 1δ (Non Patent Literature 13).

That is to say, the fact that, as the present inventors have done, somebody has focused on the therapeutic usefulness of a compound having inhibitory action highly selective to casein kinase 1, wherein with regard to their selective inhibition against isoforms, the compound has selective inhibitory action against casein kinase 1δ and casein kinase 1ε, and somebody has then conducted intensive studies directed towards searching for a compound of interest, has not been known so far.

In order to achieve the above-mentioned object, the present inventors have constructed a complex model based on information of the three-dimensional structures of casein kinase 1δ and other similar proteins, for the purpose of finding various compounds having inhibitory action against the phosphorylation ability of casein kinase 1δ and casein kinase 1ε. Then, the inventors have performed virtual screening, using DOCK4, in which consensus score has been introduced into commercially available compound database (wherein information of the three-dimensional structure of casein kinase 1δ has been known by registration in the Protein Data Bank, etc. (Non Patent Literature 14)), so that they have narrowed compounds. The inventors have purchased or have newly synthesized these compounds, and thereafter, they have practically performed the screening of the compounds for biological activity.

As a result, the present inventors have found that a compound represented by a general formula (1) as shown below has inhibitory action against the phosphorylation ability of casein kinase 1δ and casein kinase 1ε. Moreover, the inventors have found that this compound has highly selective inhibitory action, which had not been known so far. Thus, the inventors have revealed that this compound is useful as an active ingredient of pharmaceutical agents for treating the above-mentioned diseases. The present invention has been completed based on these findings.

That is to say, the present invention relates to an oxazolone derivative represented by a general formula (1) as shown below having inhibitory action against casein kinase 1δ and casein kinase 1ε, a pharmacologically acceptable salt thereof, a solvate thereof, or a hydrate thereof.

[Formula 1]

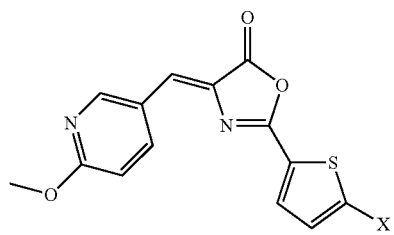

(1)

wherein X represents a halogen atom (which may be any one of a fluorine atom, a chlorine atom, a bromine atom, and an iodine atom).

Moreover, the present invention relates to an inhibitor of casein kinase 1δ and casein kinase 1ε, which comprises, as an active ingredient, the oxazolone derivative represented by the above general formula (1), the pharmacologically acceptable salt thereof, the solvate thereof or the hydrate thereof.

Furthermore, the present invention relates to a pharmaceutical agent useful for the treatment and/or prevention of diseases, with the development process of the pathological conditions of which the activation of casein kinase 1δ or casein kinase 1ε is associated, wherein the pharmaceutical agent comprises, as an active ingredient, the oxazolone derivative represented by the above general formula (1), the pharmacologically acceptable salt thereof the solvate thereof, or the hydrate thereof. Further, the present invention relates to a pharmaceutical agent for the treatment and/or prevention of circadian rhythm disorder (including sleep disorder), central neurodegenerative disease, and cancer, wherein the pharmaceutical agent comprises, as an active ingredient, the oxazolone derivative represented by the above general formula (1), the pharmacologically acceptable salt thereof the solvate thereof, or the hydrate thereof.

Still further, the present invention relates to a method for treating diseases, with the pathological conditions of which the activation mechanism of casein kinase 1δ or casein kinase 1ε is associated, wherein the method comprises administering the above-described pharmaceutical agent to a patient.

Advantageous Effects of Invention

The compound of the present invention can inhibit the activity of casein kinase 1δ and casein kinase 1ε. As a result, the present compound can treat diseases, with the pathological conditions of which the activation mechanism of the casein kinase 1δ or casein kinase 1ε is associated.

The compound of the present invention and the pharmaceutical agent of the present invention comprising the aforementioned compound as a pharmaceutically active ingredient can be used to treat diseases, with the pathological conditions of which the activation mechanism of the casein kinase 1δ or casein kinase 1ε is associated.

The compound of the present invention and the pharmaceutical agent of the present invention comprising the aforementioned compound as a pharmaceutically active ingredient have higher selectivity to the casein kinase 1δ and casein kinase 1ε than those of conventional compounds having casein kinase 1 inhibitory activity. As a result, the compound of the present invention and the pharmaceutical agent of the present invention comprising the aforementioned compound as a pharmaceutically active ingredient can be anticipated to have higher clinical efficiency than that of existing compounds, on diseases, with the pathological conditions the activation mechanism of casein kinase 1δ or casein kinase 1ε is associated. At the same time, the compound of the present invention and the pharmaceutical agent of the present invention comprising the aforementioned compound as a pharmaceutically active ingredient can be anticipated to have higher safety than that of existing compounds.

DESCRIPTION OF EMBODIMENTS

A preferred embodiment of the present invention relates to the oxazolone derivative represented by the general formula (1), the pharmacologically acceptable salt thereof, the solvate thereof, or the hydrate thereof. This compound has inhibitory action against casein kinase 1δ or casein kinase 1ε.

The compound represented by the general formula (1) has been newly synthesized in the present invention. Moreover, the present invention has disclosed for the first time that the compound represented by the general formula (1) has activity of inhibiting the activity of casein kinase 1δ or casein kinase 1ε. The novel oxazolone derivative represented by the general formula (1) of the present invention can be produced using a chemical synthetic method described in the after-mentioned Examples.

The inhibitor of casein kinase 1δ or casein kinase 1ε and the oxazolone derivative represented by the general formula (1) comprised as an active ingredient in the pharmaceutical agent according to the present invention include their tautomers and geometric isomers (e.g. E form, Z form, etc.), unless otherwise specified. Further, enantiomers are also included in the scope of the present invention, if they are present.

The types of the compound represented by the general formula (1), the salt thereof, and the hydrate thereof are not limited. Examples include the following compounds:

4-((6-methoxy-3-pyridinyl)methylene)-2-(5-fluoro-2-thienyl)-5(4H)-oxazolone, an acceptable salt thereof, and a hydrate thereof;

4-((6-methoxy-3-pyridinyl)methylene)-2-(5-chloro-2-thienyl)-5(4H)-oxazolone, an acceptable salt thereof, and a hydrate thereof;

4-((6-methoxy-3-pyridinyl)methylene)-2-(5-bromo-2-thienyl)-5(4H)-oxazolone, an acceptable salt thereof, and a hydrate thereof; and 4-((6-methoxy-3-pyridinyl)methylene)-2-(5-iodo-2-thienyl)-5(4H)-oxazolone, an acceptable salt thereof, and a hydrate thereof.

According to another preferred embodiment of the present invention, there is provided an inhibitor of casein kinase 1δ and casein kinase 1ε, which comprises, as an active ingredient, the oxazolone derivative represented by the general formula (1), the pharmacologically acceptable salt thereof, the solvate thereof, or the hydrate thereof. According to a further preferred embodiment of the present invention, there is provided a pharmaceutical agent for treating diseases, with the pathological conditions of which the activation of casein kinase 1δ or casein kinase 1ε is associated, and particularly, circadian rhythm disorder (including sleep disorder), central neurodegenerative disease, and cancer, wherein the pharmaceutical agent comprises the above-described compound as a pharmacologically active ingredient.

The casein kinase 1δ in the present invention may be called with similar names or alias names, such as "Casein Kinase 1 delta," "Casein kinase 1 isoform delta," "CK1(-) delta," "CK1d", "HCKID," "Casein Kinase 1δ," "casein kinase 1 isoform δ," and "CK1(-)δ." In the present invention, casein kinase 1δ means a protein comprising an amino acid sequence that is identical to or substantially identical to the amino acid sequences registered under registration Nos. NP_001884.2, NP_620693.1, NP_620690.1 and NP_082150.1 in the database of NCBI Reference Sequences (RefSeq) published by the National Center for Biotechnology information (NCBI).

Herein, the "protein comprising an ammo acid sequence that is substantially identical to . . . " means a protein, which comprises an amino acid sequence having identity of approximately 60% or more preferably approximately 70% or more, more preferably approximately 80%, 81%, 82%, 83%, 84%, 85%, 86%, 87%, 88%, 89%, 90%, 91%, 92%, 93%, 94%, 95%, 96%, 97% or 98%, and most preferably approximately 99%, at the amino acid sequence level with the above-described amino acid sequences having RefSeq Nos. NP_001884.2, NP_620693.1, NP_620690.1 and NP_082150.1 and which has the activity of protein phosphorylation enzyme.

Otherwise, the protein comprising an amino acid sequence substantially identical to the amino acid sequences having RefSeq Nos. NP_001884.2, NP_620693.1, NP_620690.1, NP_082150.1 is a protein, which consists of an amino acid sequence comprising as deletion, substitution or addition of one or several (preferabl) about 1 to 30, more preferably about 1 to 10, and further preferably 1 to 5) amino acids with respect to the amino acid sequences having RefSeq Nos. NP_001884.2, NP_620693.1, NP_620690.1 and NP_082150.1, and which the activity of protein phosphorylation enzyme.

The casein kinase 1ε in the present invention may be called with similar names or alias names, such as "Casein Kinase 1 epsilon," "Casein kinase 1 isoform epsilon," "CK1(-) epsilon," "CK1e", "HCKIE," "Casein Kinase 1ε," "casein kinase 1 isoform ε," and "CK1(-)ε." In the present invention, casein kinase 1ε means a protein comprising an amino acid sequence that is identical to or substantially identical to the amino acid sequences registered tinder registration Nos. NP_001885.1, NP_689407.1 and NP_038795.3 in the database of NCBI Reference Sequences (RefSeq) published by the National Center for Biotechnology Information (NCBI).

Herein, the "protein comprising an amino acid sequence that is substantially identical to . . . " means a protein, which comprises an amino acid sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97% or 98%, and most preferably approximately 99%, at the amino acid sequence level with the above-described amino acid sequences having RefSeq Nos. NP_001885.1, NP_689407.1 and NP_38795.3, and which has the activity of protein phosphorylation enzyme.

Otherwise, the protein comprising an amino acid sequence substantially identical to the amino acid sequences having RefSeq Nos. Np_001885.1, NP_689407.1 and NP_038795.3 is a protein, which consists of an amino acid sequence comprising a deletion, substitution or addition of one or several (preferably about 1 to 30, more preferably about 1 to 10, and further preferably 1 to 5) amino acids with respect to the amino acid sequences having RefSeq Nos. NP_001885.1, NP_689407.1 and NP_038795.3, and which the activity of protein phosphorylation enzyme.

The diseases, with the pathological conditions of which the activation mechanism of casein kinase 1δ or casein kinase 1ε associated, are not limited. Examples of such diseases include circadian rhythm disorder (including sleep disorder), neurodegenerative disease, and cancer.

In the present specification, the type of circadian rhythm disorder is not limited. The circadian rhythm disorder includes mood disorder and sleep disorder. Such sleep disorder is circadian rhythm sleep disorder, and the circadian rhythm sleep disorder includes a disease selected from the group consisting of shift work sleep disorder, jet lag syndrome, advanced sleep phase syndrome, and delayed sleep phase syndrome. Moreover, the sleep disorder includes a disease selected from the group consisting of insomnia, sleep-related breathing disorder, central hypersomnia, parasomnia, and sleep-related movement disorder. Furthermore, the above-described mood disorder is selected from either depressive disorder or bipolar disorder, and the depressive disorder is major depressive disorder. Further, the mood disorder is selected from either depressive disorder or bipolar disorder, and the bipolar disorder is selected from the group consisting of bipolar type-I disorder or bipolar type-II disorder. Still further, examples of the disease in the present invention include insomnia, sleep-related breathing disorder, central hypersomnia, circadian rhythm sleep disorder, parasomnia, sleep-related movement disorder, and sleep disorder caused by other reasons.

In the present specification, insomnia includes psychophysiologic insomnia caused by stress or the like, insomnia caused by medical disease, and the like. Sleep-related breathing disorder includes central sleep apnea syndrome, obstructive sleep apnea syndrome, sleep-related hypoventilation/anoxemia syndrome, and the like. Central hypersomnia includes narcolepsy, idiopathic hypersomnia, recurrent hypersomnia, and the like. Circadian rhythm sleep disorder includes shift work sleep disorder, jet lag syndrome, advanced sleep phase syndrome, delayed sleep phase syndrome, and the like. Parasomnia includes sleep walking, REM sleep behavior disorder, and the like. Sleep-related movement disorder includes restless legs syndrome, periodic limb movement disorder, and the like.

In the present specification, the type of neurodegenerative disease is not limited, Examples of central neurodegenerative disease include: neurodegenerative disease caused by Alzheimer's disease, Parkinson's disease or Down's syndrome; nerve degeneration caused by physical nerve damage (brain tissue damage such as brain contusion, and nerve damage caused by head injury and the like); and nerve degeneration caused by nerve damage occurred after ischemia or ischemic reperfusion include: stroke, cerebral infarction, cerebral hemorrhage, cerebral ischemia, subarachnoid hemorrhage, aneurysmal hemorrhage, myocardial infarction, hypoxia, anoxia and nerve damage caused by grand mal/cerebral ischemia.

The type of cancer that arises from the pancreas is not limited in the present specification. Examples of such cancer include pancreatic duct cancer, invasive pancreatic duct cancer, pancreatic endocrine tumor, intraductal papillary mucinous tumor, nutritious cystoma, acinar cell cancer, metastatic pancreatic cancer.

As active ingredients of the pharmaceutical agent of the present invention, in addition to the compounds represented by the above general formula (1), physiologically acceptable salts thereof may also be used. When an acidic group is present, examples of the salts that can be formed therewith include: the salts of alkaline metals and alkaline-earth metals such as lithium, sodium, potassium, magnesium and calcium; the salts of amines such as ammonia, methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methyl glucamine and L-glucamine; and salts formed with basic amino acids such as lysine, δ-hydroxylysine and arginine. When a basic group is present, examples of the salts that can be formed therewith include: salts with mineral acids such as hydrochloric acid, hydrobromic acid, sulfuric acid, nitric acid and phosphoric acid; salts with organic acids such as methanesulfonic acid, benzenesulfonic acid, paratoluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid and salicylic acid: and salts with acidic amino acids such as aspartic acid and glutamic acid.

Furthermore, as active ingredients of the pharmaceutical agent of the present invention, the solvates or hydrates of the compounds represented by the above general formula (1) or the salts thereof may also be used.

With regard to the pharmaceutical agent of the present invention, the compounds represented by the above general formula (1), the pharmacologically acceptable salts thereof, the solvates thereof or the hydrates thereof, which are contained as active ingredients, may be directly administered. In general, however, it is desired to administer the pharmaceutical agent of the present invention in the form of a pharmaceutical composition comprising, the above-mentioned substance as an active ingredient and one or two or more pharmaceutical additives. As an active ingredient of the pharmaceutical agent of the present invention, two or more types of the above-mentioned substances may be used in combination. It is also possible to mix into the above-described pharmaceutical composition, the active ingredients of other pharmaceutical agents for treating and/or preventing diseases with the pathological conditions of which the activation mechanism of casein kinase 1δ or casein kinase 1ε is associated. It is also possible to mix into the above-described pharmaceutical composition, the active ingredients of other pharmaceutical agents for treating and/or preventing circadian rhythm disorder (including sleep disorder), central neurodegenerative disease and cancer, among the aforementioned diseases.

The type of a pharmaceutical composition is not particularly limited. Examples of a dosage form include a tablet, a capsule, a granule, a powder, a syrup, a suspending agent, a suppository, an ointment, a cream agent, a gel agent, a patch, an inhalant, and an injection. These pharmaceutical agents are prepared in accordance with ordinary methods. It is to be noted that a liquid agent may adopt a dosage form in which the agent is dissolved or suspended in water or a suitable solvent when used. In addition, a tablet or a granule may be coated according to well known methods. In the case of an injection, it is prepared by dissolving the compound of the present invention in water. The compound of the present invention may also be dissolved in a normal saline or a glucose solution, as necessary. Otherwise, a buffer or a preservative may also be added to the present compound. The pharmaceutical agent of the present invention is provided in the form of any given pharmaceutical agent for use in oral administration or parenteral administration. For example, it can be prepared in the form of: pharmaceutical compositions for oral administration, such as a granule, a fine grain agent, a powder, a hard capsule, a soft capsule, a syrup, an emulsion, a suspending agent or a liquid agent; and pharmaceutical compositions for parenteral administration, such as an injection for intravenous administration, intramuscular administration or subcutaneous administration, a drop, a transdermal agent, a transmucosal agent, a nasal drop, an inhalant, or a suppository. An injection, a drop or the like may be prepared in the dosage form of freeze-dried powders, and the powders may be then dissolved in a suitable aqueous medium such as a normal saline when used. Moreover, it is also possible that a sustained release agent coated with macromolecules and the like is directly administered into the brain.

The types of pharmaceutical additives used in the production of the pharmaceutical composition, the ratio of such pharmaceutical additives to the active ingredient, or a method for producing a pharmaceutical composition can be appropriately selected by a person skilled in the art, depending on the form of the composition. As pharmaceutical additives, inorganic or organic substances, or solid or liquid substances can be used. In general, such pharmaceutical additives can be mixed in a weight: percentage amount from 1% to 90% with respect to the weight of the active ingredient. Specific examples of such a substance include lactose, glucose, mannit, dextrin, cyclodextrin, starch, sucrose, magnesium aluminometasilicate, synthetic aluminum silicate, carboxymethylcellulose sodium, hydroxypropyl starch, carboxymethylcellulose calcium, ion exchange resin, methyl cellulose, gelatin, gum arabic, hydroxypropyl cellulose, hydroxypropylmethyl cellulose, polyvinylpyrrolidone, polyvinyl alcohol, light anhydrous silicic acid, magnesium stearate, talc, Tragaranth, bentonite, veegum, titanium oxide, sorbitan fatty acid ester, sodium lauryl sulfate, glycerin, fatty acid glycerin ester, purified lanolin, glycerinated gelatin, polysorbate, macrogol, vegetable oil, wax, liquid paraffin, white petrolatum, fluorocarbon, nonionic surfactant, propylene glycol, and water.

In order to produce a solid agent for oral administration, an active ingredient is mixed with an excipient such as lactose, starch, crystalline cellulose, calcium lactate or silicic acid anhydride to form a powder agent. Otherwise, if necessary, a binder such as saccharose, hydroxypropyl cellulose or polyvinylpyrrolidone, a disintegrator such as carboxymethyl cellulose or carobxymethylcellulose calcium, and other additives are further added to the mixture, and the obtained mixture is then subjected to a dry or wet granulating method, so as to form a granule agent. Moreover, in order to produce a tablet, such a powder agent or a granule agent may be subjected to direct tableting, or a lubricant such as magnesium stearate or talc may be added to the powder agent or granule agent and the obtained mixture may be then subjected to tableting. Such a granule agent or a tablet may be coated with an enteric coating base such as hydroxypropylmethyl cellulose phthalate or a methacrylic acid-methyl methacrylate polymer, so as to prepare an enteric-coated agent. Alternatively, such a granule agent or a tablet may also be coated with ethyl cellulose, carnauba wax, hydrogenated oil or the like, so as to prepare a sustained release agent. Furthermore, in order to produce a capsule, a powder agent or a granule agent is filled into a hard capsule. Otherwise, the active ingredient is directly coated with a gelatin film, or it is dissolved in glycerin, polyethylene glycol, sesame oil, olive oil or the like and is then coated with a gelatin film, so as to prepare a soft capsule.

In order to produce an injection, the active ingredient, and as necessary, a pH adjuster such as hydrochloric acid, sodium hydroxide, lactose, lactic acid, sodium, sodium monohydrogen phosphate or sodium dihydrogen phosphate, an isotonizing agent such as sodium chloride or glucose, and other additives, are dissolved in distilled water for injection, and the obtained solution is then subjected to aseptic filtration and is then filled into an ampule. Otherwise mannitol, dextrin, cyclodextrin, gelatin and the like are added to the obtained solution, followed by vacuum-freeze drying, so as to prepare an injection that is to be dissolved when used. Moreover, lecithin, polysorbate 80, polyoxyethylene hydrogenated castor oil or the like is added to the active ingredient to emulsify it in water, so as to prepare an emulsion for injection.

In order to produce an agent for rectal administration, the active ingredient, together with a suppository base material such as cacao butter, fatty acid tri-, di- and mono-glycerides, or polyethylene glycol, is dissolved by humidification, and the obtained solution is then poured into as mold, followed by cooling. Otherwise, the active ingredient is dissolved in polyethylene glycol, soybean oil or the like, and the obtained solution is then coated with a gelatin film.

In order to produce an external agent for skin, the active ingredient is added to white petrolatum, beeswax, liquid paraffin, polyethylene glycol or the like, and the mixture is humidified if necessary, and it is then kneaded, so as to prepare an ointment. Otherwise, the active ingredient is kneaded together with an adhesive such as rosin or an alkyl acrylate polymer, and the obtained mixture is then expanded on a non-woven fabric such as polyalkyl, so as to prepare a tape agent.

The applied dose and number of doses of the pharmaceutical agent of the present invention are not particularly limited. The applied dose and the number of doses can be selected, as appropriate, by a doctor's decision, depending on various conditions such as the purpose of prevention and/or treatment of deterioration and progression of a target disease, the type of the disease, the body weight, age and other conditions of a patient, etc. In general, the applied dose is approximately 0.01 to 1000 mg (the weight of the active ingredient) per adult per day via oral administration. Such a dose can be administered once or divided over several administrations per day, or every several days. When the pharmaceutical agent of the present invention is used as an injection, it is desired that a dose of 0.01 to 100 mg (the weight of the active ingredient) is administered per adult per day continuously or intermittently.

Using a carrier capable of preventing the immediate elimination of an agent from the inside of a body, the pharmaceutical agent of the present invention can be prepared in the form of a sustained release agent such as an implanted tablet or a delivery system encapsulated into a microcapsule. For example, there can be used biodegradable biocompatible polymers such as ethylene vinyl acetate, polyacid anhydride, polyglycolic acid, collagen, polyorthoester, and polylacetic acid. Such materials can be easily prepared by a person skilled in the art. In addition, as liposome suspension can also be used as a pharmaceutically acceptable carrier. The type of an available liposome is not limited. The liposome can be prepared as a lipid composition containing phosphatidyl choline, cholesterol and a PEG derivative of phosphatidylethanol (PEG-PE) to a size suitable for use, by passing it through a filter with an appropriate pore size, and it is then purified by a reverse-phase evaporation method.

The pharmaceutical agent of the present invention can be prepared as a pharmaceutical composition, and it can be included in a vessel or pack, together with an administration manual, so as to prepare a kit. When the pharmaceutical composition according to the present invention is provided as a kit, different constituents contained in the pharmaceutical composition are wrapped with different vessels, and they are then mixed immediately before use. Thus, the constituents are individually wrapped because it enables long-term storage without losing the functions of active constituents.

A reagent contained in the kit is supplied into a certain type of vessel, in which constituents maintain their activity for a long period of time and they are not adsorbed on the material of the vessel and are not degraded. For instance, a sealed glass ampule contains a buffer that has been wrapped under neutral non-reactive gas such as nitrogen gas. The ampule is made of glass, an organic polymer such as polycarbonate or polystyrene, ceramic, metal, other suitable materials that are commonly used to retain the reagent, and the like. Examples of other suitable vessels include a simple bottle produced from similar substances for ampule, and a wrapping material, the inside of which is lined with aluminum or alloy foil. Other vessels include a test tube, a vial, a flask, a bottle, a syringe, and a similar product thereof. The vessel has an aseptic access port, such as a bottle having a stopper that is penetrable with a subcutaneous injection needle.

In addition, an instruction manual is attached to the kit. The instruction manual for the kit consisting of the present pharmaceutical composition is printed on a paper or other materials, and/or it may be supplied as an electrically or electromagnetically readable medium, such as a floppy (registered trademark) disk, CD-ROM, DVD-ROM, a Zip disk, a video tape, or an audio tape. A detailed instruction manual may be actually attached into the kit, or it may be published on a website which is designated by a kit manufacturer or distributer and is then noticed via an electric mail.

Moreover, the present invention provides a therapeutic method for treating a target disease by administering to a patient, a pharmaceutical agent or a pharmaceutical composition, which comprises, as an active ingredient, the compound represented by the general formula (1) of the present invention, the pharmacologically acceptable salt thereof, the solvate thereof, or the hydrate thereof.

Herein, the term "treatment" is used to mean that the progression and deterioration of the pathological conditions of a disease are inhibited or alleviated in a mammal that has been affected with or is suspected to have the disease, and thereby, the term "treatment" is used to mean a therapeutic means directed towards inhibiting or alleviating the progression and deterioration of various symptoms of the disease.

Moreover, the term "disease" means diseases as a whole, with the pathological conditions of which the activation mechanism of casein kinase 1δ or casein kinase 1ε is associated. Thus, the type of the disease is not particularly limited. Examples of such a disease include insomnia, sleep-related breathing disorder, central hypersomnia, circadian rhythm sleep disorder, parasomnia, and sleep-related movement disorder. The sleep disorder of the circadian rhythm sleep disorder is circadian rhythm sleep disorder, and the circadian rhythm sleep disorder includes shift work sleep disorder, jet lag syndrome, advanced sleep phase syndrome, and delayed sleep phase syndrome. The mood disorder of the circadian rhythm disorder includes depressive disorder and bipolar disorder. In addition, the concerned disease also includes: neurodegenerative disease caused by Alzheimer's disease, Parkinson's disease or Down's syndrome; central neurodegenerative disease caused by cerebrovascular disorder; cancer as a whole, the type of which is not specified; and particularly, cancer derived from the pancreas, such as pancreatic duct cancer, invasive pancreatic duct cancer, pancreatic endocrine tumor, intraductal papillary mucinous tumor, mucinous cystoma, acinar cell cancer, and metastatic pancreatic cancer.

The "mammal" as a subject in need of a treatment means any given animal classified into Mammalia, and the type of the mammal is not particularly limited, Examples of such a mammal include humans, pet animals such as a dog, a cat or a rabbit, and livestock animals such as a bovine, a swine, a sheep or a horse. A particularly preferred "mammal" is a human.

Next, the present invention will be described in specific examples. However, these examples are not intended to limit the scope of the present invention.

EXAMPLES

Example 1

4-((6-Methoxy-3-pyridinyl)methylene)-2-(5-fluoro-2-thienyl)-5(4H)-oxazolone

[Formula 2]

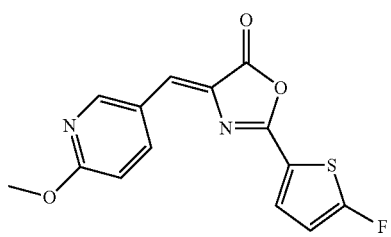

(2)

Since, in general, it is extremely difficult to introduce a fluoro group into a thiophene ring, the compound represented by the above formula (2) was attempted to be synthesized by a process shown in Scheme 1 below comprising many synthetic steps, in comparison with the synthetic method described in Examples of Japanese Patent Application No. 2009-245477. As a result, the compound of interest was successfully produced. It is to be noted that the method for synthesizing the compound represented by the formula (2) is not limited to the process shown in Scheme 1.

Scheme 1

[Formula 3]

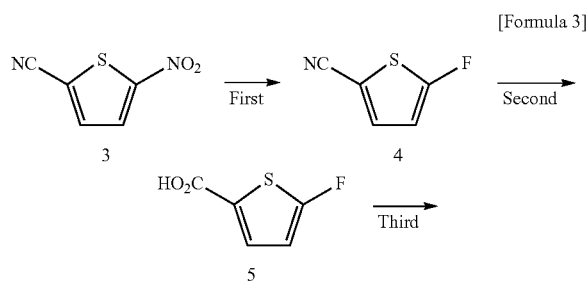

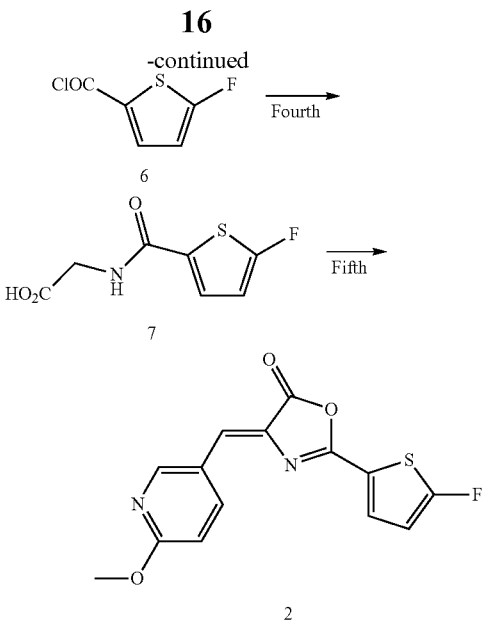

<First Step>

3.0 g of 5-nitro-2-thiophene carbonitrile (Compound 3; 19.5 mmol), 5.66 g (9.75 mmol) of potassium fluoride, 0.82 g (1.95 mmol) of tetraphenyl phosphonium bromide, 70 ml of sulfolane, and 2.81 ml (19.5 mmol) of phthaloyl dichloride were successively added to a three-necked flask, and the mixture was then stirred under heating at an internal temperature of 180° C. for 2 hours. After completion of the reaction, the reaction solution was cooled to room temperature, and 300 ml of water was then added thereto, followed by extraction with 200 ml of diethyl ether three times. Thereafter, organic layers were gathered, and the gathered organic layer was successively washed with 200 ml of 1 N sodium hydroxide twice, then with 200 ml of water, and then with 100 ml of a saturated saline. The resultant was dried over sodium sulfate, and the solvent was then removed under reduced pressure. The residue was purified by silica gel chromatography (pentane/diethyl ether=2/1), so as to obtain 150 mg of Compound 4.

<Second Step>

138 mg (1.07 mmol) of Compound 4 and 5 ml of 1 N sodium hydroxide were added to an egg plant-shaped flask, and the mixture was then stirred under heating at an external temperature of 100° C. for 2 hours. After completion of the reaction, the reaction solution was cooled to room temperature. Then, 5 ml of water was added to the reaction solution, and 10 ml of 1N hydrochloric acid was also added to the mixture, thereby resulting in pH=1. Thereafter, the mixture was extracted with 30 ml of dichloromethane twice. Subsequently, organic layers were gathered. The organic layer was dried over sodium sulfate, and the solvent was then removed under reduced pressure, so as to obtain 110 mg of Compound 5.

<Third Step>

100 mg (0.68 mmol) of Compound 5, 3 ml of thionyl chloride, and 50 µl of formamide were added to an egg plant-shaped flask, and the mixture was then stirred under heating at an external temperature of 100° C. for 2 hours. After completion of the reaction, the reaction solution was cooled to room temperature, and thionyl chloride was removed under reduced pressure, followed by azeotropy with toluene twice, so as to quantitatively obtain 112 mg of Compound 6.

<Fourth Step>

51 mg (0.68 mmol) of glycine and 1 ml of 6 N sodium hydroxide were added to an egg plant-shaped flask, and the mixture was then stirred under cooling on ice. Thereafter, 5 ml of a diethyl ether solution of Compound 6 was added to the reaction solution, and the obtained mixture was then stirred at room temperature for 3 hours. After completion of the reaction, the reaction solution was cooled on ice, and 10 ml of water was then added to the resulting solution. Then, 10 ml of 1 N hydrochloric acid was added to the solution to adjust the pH value to pH 1, and the obtained solution was then extracted with dichloromethane three times. Thereafter, organic layers were gathered. The gathered organic layer was washed with 30 ml of a saturated saline, and was then dried over sodium sulfate, followed by removing, the solvent under reduced pressure, so as to obtain 24 mg of Compound 7.

<Fifth Step>

21.7 mg (0.107 mmol) of Compound 7, 200 μl of acetic anhydride, and 65 μl of pyridine were added to an egg plant-shaped flask, and the obtained mixture was then stirred under heating at an external temperature of 100° C. for 1 hour. After completion of the reaction, the reaction solution was cooled to room temperature, and the solvent was then removed under reduced pressure. The residue was purified by preparative thin layer chromatography (toluene/diethyl ether=5/1), so as to obtain 14 mg of Compound 2 (0.046 mmol; total yield: 0.3%).

MALDI-TOFF MS calculated value $C_{14}H_9FN_2OS$, 304.03, measured value, 304.23

During the process for synthesizing Compound 2, it was extremely difficult to introduce a fluoro group into a thiophene ring in the first step, and thus, the total yield and the purity became low values. As a result, the purity of Compound 2 as a final product also became low. Thus although accuracy may not be very high, a peak obtained by measuring Compound 2 dissolved in DMSO-d6 using Nuclear Magnetic Resonance AV-500 (500 MHz) manufactured by Bunker is shown below.

$^1$H-NMR (500 MHz, DMSO-$d_6$, δ)

8.73 (s, 1H), 8.19 (d, 1H), 7.72 (m, 1H), 7.36 (d, 1H), 7.26 (m, 1H), 7.19 (s, 1H), 3.91 (s, 3H)

The compound represented by the formula (2) could be synthesized by the method shown in the above Scheme 1. However, this method was problematic in that the purity of the obtained product was low.

Thus, the present inventors conducted studies regarding other synthetic methods, and as a result, they succeeded in significantly improving the total yield and purity of a product according to a method shown in Scheme 2 below.

Scheme 2

[Formula 4]

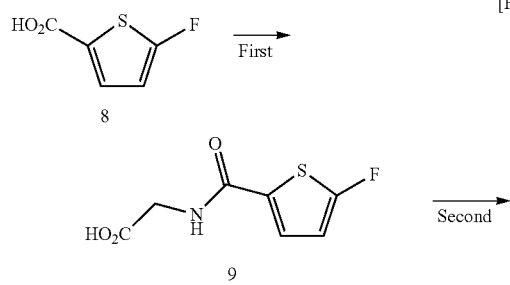

<First Step>

1.00 g of 5-fluorothiophene carboxylic acid (purity: 95%; 5.91 mmol), 1 ml (13.8 mmol) of thionyl chloride, and 10 ml of benzene were added to a three-necked flask, and the mixture was then stirred under heating at a bath temperature of 105° C. for 2 hours. Thereafter, the reaction solution was cooled to room temperature, and thionyl chloride was then removed by distillation. The residue was subjected to azeotropy with benzene and carbon tetrachloride, so as to obtain a brown oily substance. To a three-necked flask that was prepared separately, 621.0 mg (8.27 mmol) of glycine and 30 ml of 0.5 N sodium hydroxide were added, and the mixture was then stirred. To the reaction solution, the previously obtained brown oily substance was added, and the obtained mixture was then stirred at room temperature for 1 hour. After completion of the reaction, the reaction solution was cooled in an ice bath, and 1 ml of 6 N hydrochloric acid was then added to the reaction solution. A precipitated solid was collected by filtration and was then washed with 30 ml of cold water. Water contained in the solid was removed by azeotropy with acetone, and the residue was then dried under reduced pressure at room temperature, so as to obtain 432.3 mg of Compound 9 (2.13 mmol; 36.0%) in the form of a light yellow solid. As a result of performing HPLC analysis on the product, the elution time was found to be 9.04 minutes, and the purity was found to be 90%.

<Second Step>

100 mg of Compound 9 (purity: 90.0%; 0.44 mmol), 80.9 g (0.59 mmol) of 6-methoxy-3-pyridinecarbaldehyde, 102 μl (1.08 mmol) of acetic anhydride, and 100 μl (1.24 mmol) of pyridine were added to a three-necked flask, and the obtained mixture was then stirred under heating at 100° C. in an oil bath for 15 minutes. After completion of the reaction, the reaction solution was cooled at 4° C., and to precipitated solid was then dissolved in 5 ml of ethanol. Then, an insoluble matter was collected by filtration. The obtained solid was washed with ethanol, so as to obtain 40.1 mg of Compound 2 (0.13 mmol; 29.5%) in the form of a yellow solid.

The HPLC purity (absorption wavelength: 254 nm) of Compound 2 was 98.7%. Compound 2 was measured using an HPLC/ESI-LIT-TOF MS device (NanoFrontier LD), and as a result, m/z=355.0, 356.0 [M+CH$_4$O—H]$^-$ was confirmed. In addition, a peak obtained by measuring Compound 2 using Nuclear Magnetic Resonance AV-500 (500 MHz) manufactured by Bruker is shown below.

$^1$H-NMR (CDCl$_3$) δ ppm (500 MHz): 4.02 (s, 3H), 6.63 (dd, 1H, $J_{HH}$=8.4 Hz, $J_{HF}$=1.4 Hz), 6.86 (d, 1H, $J_{HH}$=8.8 Hz), 7.13 (s, 1H), 7.55 (dd, 1H, $J_{HH}$=8.4 Hz, $J_{HF}$=4.1 Hz), 8.60 (dd, 1H, $J_{HH}$=8.8 Hz, $J_{HH}$=2.3 Hz), 8.67 (d, 1H, $J_{HH}$=2.3 Hz)

$^{13}$C-NMR (CDCl$_3$) δ ppm (1.25 MHz): 53.9, 110.0, 110.1, 111.8, 117.4, 117.5, 123.5, 127.6, 130.6, 130.6, 131.7, 140.9, 152.1, 158.2, 165.3, 166.5, 169.4, 171.8

Considering the HPLC purity that was 98.7%, the mass spectrometry, and the NMR spectral pattern, the thus synthesized compound is supported to be Compound 2.

As described above, by applying the synthetic method of Scheme 2, the total number of steps could be reduced from 5 to 3 in comparison with the case of Scheme 1, and further, the total yield could be increased by approximately 7 times and the purity of Compound 2 as a final product could also be significantly improved. From these results, it is considered that the door would be opened to the possibility of stable supply of the compound.

Example 2

4-((6-Methoxy-3-pyridinyl)methylene)-2-(5-chloro-2-thienyl)-5(4H)-oxazolone

[Formula 5]

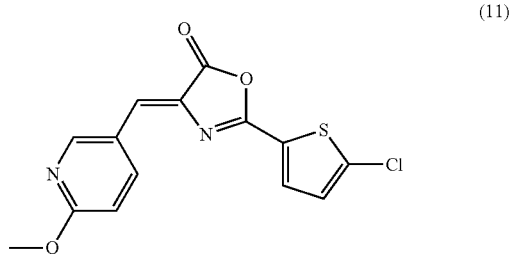

(11)

In addition to the compound represented by the formula (2) into which a fluoro group has been introduced, the compound represented by the above formula (11), into which a chloro group has been introduced, was also produced. It is to be noted that the method for synthesizing the compound represented by the formula (11), into which a chloro group has been introduced, is not limited to a process shown in Scheme 3 below.

Scheme 3

[Formula 6]

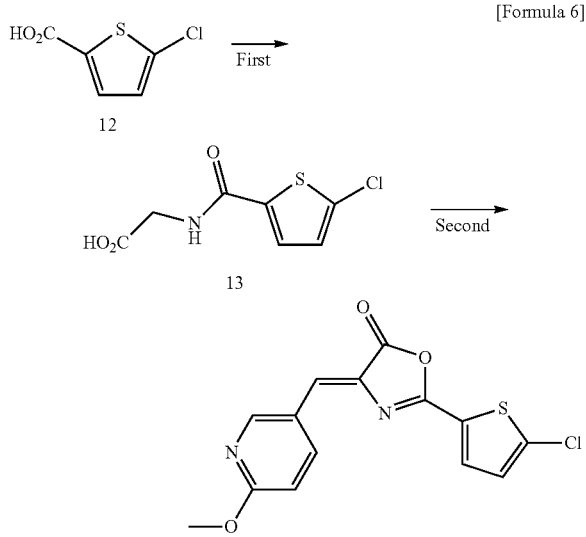

<First Step>

1.00 g (6.15 mmol) of 5-chlorothiophene carboxylic acid, 1 ml (13.8 mmol) of thionyl chloride, and 10 ml of benzene were added to a three-necked flask, and the mixture was then stirred under heating at a bath temperature of 1.05° C. for 2 hours. Thereafter, the reaction solution was cooled to room temperature, and thionyl chloride was then removed by distillation. The residue was subjected to azeotropy with benzene and carbon tetrachloride, so as to obtain a brown oily substance.

To a three-necked flask that was prepared separately, 323.2 mg (4.31 mmol) of glycine and 15 ml of 0.5 N sodium hydroxide were added, and the mixture was then stirred. To the reaction solution, the previously obtained brown oily substance was added, and the obtained mixture was then stirred at room temperature for 1 hour. After completion of the reaction, the reaction solution was cooled in an ice bath. Thereafter, 1 ml of 6 N hydrochloric acid was added to the reaction solution. A precipitated solid was collected by filtration and was then washed with 30 ml of cold water. The solid was dried under reduced pressure at room temperature, so as to obtain 386.2 mg of Compound 13 (1.76 mmol; 53%) in the form of a light yellow solid. As a result of performing HPLC analysis on the product, the elution time was found to be 10.06 minutes, and the purity was found to be 99.5% or more.

<Second Step>

100 mg (0.46 mmol) of Compound 13, 73.9 g (0.54 mmol) of 6-methoxy-3-pyridinecarbaldehyde, 102 μl (1.08 mmol) of acetic anhydride, 48 μl (0.59 mmol) of pyridine, and 1 ml of 1,4-dioxane were added to as three-necked flask, and the obtained mixture was then stirred under heating at 100° C. in an oil bath for 15 minutes. After completion of the reaction, the reaction solution was cooled at 4° C., and a precipitated solid was then dissolved in 5 ml of ethanol. Then, an insoluble matter was collected by filtration. The obtained solid was washed with ethanol, so as to obtain 10.1 mg of Compound 11 (0.031 mmol; 6.0%) in the form of a yellow solid.

The HPLC purity (absorption wavelength: 254 nm) of Compound 11 was 99.5%. Compound 11 was measured using an HPLC/ESI-LIT-TOF MS device (NanoFrontier LD), and as a result, m/z=351.0, 352.0 [M+CH$_4$O—H]$^-$ was confirmed. In addition, a peak obtained by measuring Compound 11 using Nuclear Magnetic Resonance AV-500 (500 MHz) manufactured by Brunker is shown below.

$^1$H-NMR(CDCl$_3$) δ ppm (500 MHz); 4.02 (s, 3H), 6.86 (d, 1H, J$_{HH}$=8.8 Hz), 7.03 (s, 1H), 7.65 (d, 1H, J$_{HH}$=4.1 Hz), 8.62 (dd, 1H, J$_{HH}$=8.7 Hz, J$_{HH}$2.4 Hz), 8.67 (d, 1H, J$_{HH}$=2.4 Hz)

$^{13}$C-NMR (CDCl$_3$) δ ppm (125 MHz): 54.0, 111.8, 123.6, 126.7, 126.9, 128.0, 128.1, 131.7, 132.2, 140.9, 151.2, 157.7, 165.4, 166.5

Considering the HPLC purity that was 99.5% or more, the mass spectrometry, and the NMR spectral pattern, the thus synthesized compound is supported to be Compound 11.

Example 3

4-((6-Methoxy-3-pyridinyl)methylene-2-(5-bromo-2-thienyl)-5(4H)-oxazolone

[Formula 7]

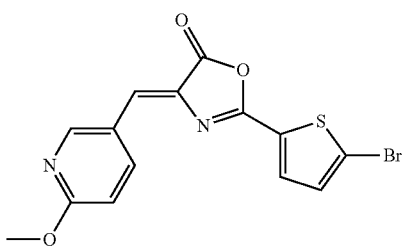 [SMILES: COc1ccc(/C=C2\N=C(c3ccc(Br)s3)OC2=O)cn1]

(14)

In addition to the compound represented by the formula (2) into which a fluoro group has been introduced, the compound represented by the above formula (14), into which a bromo group has been introduced, was also produced. It is to be noted that the method for synthesizing the compound represented by the formula (14), into which a bromo group has been introduced, is not limited to a process shown in Scheme 4 below.

Scheme 4

[Formula 8]

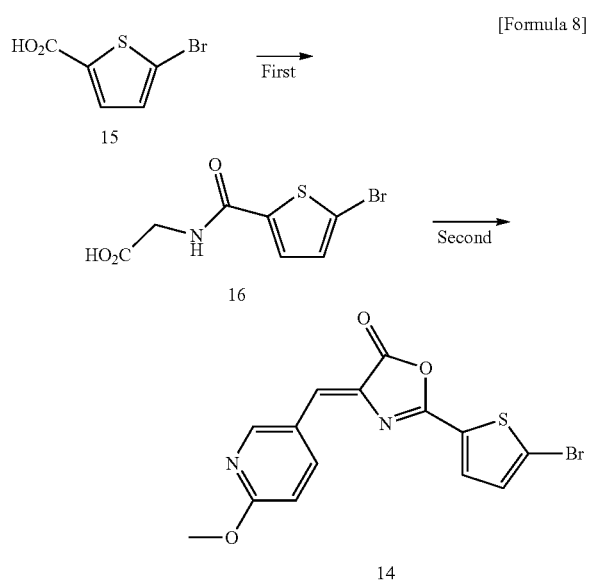

<First Step>

1.00 g (4.83 mmol) of 5-bromothiophene carboxylic acid, 5 ml (68.9 mmol) of thionyl chloride, and 4 ml of benzene were added to a three-necked flask, and the mixture was then stirred under heating at a bath temperature of 105° C. for 2 hours. Thereafter, the reaction solution was cooled to room temperature, and thionyl chloride was then removed by distillation. The residue was subjected to azeotropy with benzene and carbon tetrachloride, so as to obtain a brown oily substance.

To as three-necked flask that was prepared separately, 412.9 mg (5.80 mmol) of glycine and 5 ml of 6 N sodium hydroxide were added, and the mixture was then stirred. To the reaction solution, the previously obtained brown oily substance was added, and the obtained mixture was then stirred at room temperature for 1 hour. After completion of the reaction, the reaction solution was cooled in an ice bath. Thereafter, 1 ml of 6 N hydrochloric acid was added to the reaction solution. A precipitated solid was collected by filtration and was then washed with 30 ml of cold water. Water contained in the solid was removed by azeotropy with acetone, and the residue was dried under reduced pressure at room temperature, so as to obtain 492.6 mg of Compound 16 (0.19 mmol; 39.0%) in the form of a light yellow solid. As a result of performing HPLC analysis on the product, the elution time was found to be 10.39 minutes, and the purity was found to be 99.7%.

<Second Step>

242.7 mg (0.92 mmol) of Compound 16, 138.1 mg (1.01 mmol) of 6-methoxy-3-pyridinecarbaldehyde, 1 ml (10.6 mmol) of acetic anhydride, and 350 μl (1.24 mmol) of pyridine were added to a three-necked flask, and the obtained mixture was then stirred under heating at 100° C. in an oil bath for 15 minutes. After completion of the reaction, the reaction solution was cooled at 4° C., and a precipitated solid was then dissolved in 5 ml of ethanol. Then, an insoluble matter was collected by filtration. The obtained solid was washed with ethanol, so as to obtain 32.2 mg of Compound 14 (0.088 mmol: 10.0%) in the form of a yellow solid.

The HPLC purity (absorption wavelength: 254 nm) of Compound 14 was 95.8%. Compound 14 was measured using an HPLC/ESI-LIT-TOF MS device (NanoFrontier LD), and as a result, m/z=m/z=396.9, 397.9 [M+CH$_4$O—H]$^-$ was confirmed. In addition, a peak obtained by measuring Compound 14 using Nuclear Magnetic Resonance AV-500 (500 MHz) manufactured by Bunker is shown below.

$^1$H-NMR(CDCl$_3$) δ ppm (500 MHz): 4.02 (s, 3H), 6.86 (d, 1H, J$_{HH}$=8.8 Hz), 7.17 (s, 1H), 7.17 (d, 1H, J$_{HH}$=4.0 Hz), 7.60 (d, 1H, J$_{HH}$4.0 Hz), 8.63 (dd, 1H, J$_{HH}$=8.8 Hz, J$_{HH}$=2.4 Hz), 8.67 (d, 1H, J$_{HH}$=2.4 Hz)

$^{13}$C-NMR (CDCl$_3$) δ ppm (125 MHz): 54.0, 111.8, 121.5, 123.6, 128.2, 129.9, 131.7, 131.7, 132.8, 140.9, 152.2, 157.6, 165.4, 166.5

Considering the HPLC purity that was 95.8%, the mass spectrometry, and the NMR spectral pattern, the thus synthesized compound is supported to be Compound 14.

In terms of the solubility of each compound in a DMSO solution, a comparison was made among the compound represented by the Formula (2), the compounds represented by the formulae (11) and (14), and a compound in which a halogen atom or the like has not been introduced into the thiophene ring of the compound of the formula (2) (4-((6-methoxy-3-pyridinyl)methylene)-2-(2-thienyl)-5(4H)-oxazolone). The compound represented by the formula (2) and the compounds represented by the formulae (11) and (14) were easily dissolved in final concentrations of 35 mM, 10 mM and 20 mM, respectively, in the DMSO solution. On the other hand, the compound in which a halogen atom or the like has not been introduced into the thiophene ring of the compound of the formula (2) was dissolved in a final concentration of 10 mM in the DMSO solution by being intensively stirred. These results could demonstrate that the compound represented by the formula (2) and the compounds represented by the formulae (11) and (14) have an improved solubility, in comparison with the casein kinase 1δ or casein kinase 1ε selective inhibitor of the prior art technique.

EXPERIMENTAL EXAMPLES

1. Casein Kinase 1δ and Casein Kinase 1ε Inhibitory Action of Oxazolone Derivative The activity of the present compound to inhibit casein kinase 1δ and casein kinase 1ε was measured using human recombinant casein kinase 1δ (INVITROGEN; Cat No. PV3665) or human recombinant casein kinase 1ε (INVITROGEN; Cat No. PV3500) as an enzyme source, and also using Z'-LYTE Ser/Thr 11 Peptide (INVITROGEN; Cat No. PV3671) as a phosphorylation substrate. The composition (final concentration) applied during each inhibitory activity measurement assay is as follows.

The present compound was previously allowed to react with the enzyme at room temperature, for 15 minutes. Two hours later, the remaining phosphorylation activity was measured using Z'-LYTE Kinase Assay Kit-Ser/Thr 11 Peptide (INVITROGEN; Cat No. PV3670).

The inhibition percentage of the present compound against the phosphotylation activity of each of casein kinase 1δ and casein kinase 1ε to which the present compound had not been added, was calculated. As a result, it was found that the compound of the formula (2) obtained by the above-described Scheme 1 had low purity, but it exhibited significant inhibitory activity against casein kinase 1δ and casein kinase 1ε under the above-mentioned conditions. The high-purity compound of the formula (2) obtained by Scheme 2 and the compound represented by the formulae (11) and (14) exhibited high inhibitory activity against casein kinase 1δ and casein kinase 1ε, as shown in Table 1 below.

TABLE 1

| Structural formula | Compound name | Casein kinase 1δ inhibition percentage | Casein kinase 1ε inhibition percentage |
| --- | --- | --- | --- |
| Formula (2) | 4-((6-Methoxy-3-pyridinyl)methylene)-2-(5-fluoro-2-thienyl)-5(4H)-oxazolone | 83.0% | 97.7% |
| Formula (11) | 4-((6-Methoxy-3-pyridinyl)methylene)-2-(5-chloro-2-thienyl)-5(4H)-oxazolone | 77.9% | 94.8% |
| Formula (14) | 4-((6-Methoxy-3-pyridinyl)methylene)-2-(5-bromo-2-thienyl)-5(4H)-oxazolone | 77.8% | 95.0% |

Assay for Casein Kinase 1δ

3.0 μg/ml or 1.0 μg/ml casein kinase 1δ, 0.3 μg/ml the present compound, 1.0 μM Peptide, 20 μM ATP, 50 mM HEPES (pH 7.4), 10 mM $MgCl_2$, 0.01% Brij-35, and 0.5% DMSO Assay for Casein Kinase 1ε

0.5 μg/ml casein kinase 1ε, 0.3 μg/ml the present compound, 1.0 μM Peptide, 20 μM ATP, 50 mM HEPES (pH 7.4), 10 mM $MgCl_2$, 0.01% Brij-35, and 0.5% DMSO The inhibitory specificity of the casein kinase 1δ to and casein kinase 1ε inhibiting compounds to various types of kinases can be examined using Profiler Pro kit (manufactured by Caliper Life Sciences) in accordance with the method described in an instruction manual included therewith. The compounds represented by the formulae (2), (11) and (14) were each allowed to react with various types of kinases for 15 minutes, resulting in the final concentration of 10 μM, 1 μM or 0.1 μM. After completion of the reaction, enzyme activity was examined. As a result, it was found that the compounds of the formulae (2), (11) and (14) did not have significant inhibitory activity against various types of kinases causing concerns about the expression of side effects such as cell growth suppression due to enzyme inhibition (MAP-KAPK2, AurA, PKCζ, RSK1, PRAK, Erk1, PKD2, CHK1, ABL, FYN, LYN, CHK2, MET, LCK, SRC, GSK3β, Erk2, PKA, AKT2, INSR, p38α, AKT1, MSK1, PKCβ2, ROCK2, CDK2, MST2, PKG1α, PAK2, IGF1R, FGFR1, MARK1, CAMK2δ, PIM2, BTK, c-TAK1, CAMK4, AMPK, FLT3, HGK, VEGFR2, KDR, c-RAF, p70S6K, IRAK4, SGK1, and SYK). Consequently, it could be concluded that the present compounds are highly selective inhibitory compounds against casein kinase 1δ and casein kinase 1ε.

On the other hand, the present inventors have found that, when the compounds of the formulae (2), (11) and (14) were each added in a concentration of 1 μM to Dual specificity tyrosine-phosphorylation-regulated kinase 1A (DYRK1A) by applying the method of the Profiler Pro kit (manufactured by Caliper Life Sciences), they inhibited the enzyme activity of DYRK1A at inhibition percentages of 65%, 78% and 85%, respectively, although their inhibitory effects against DYRK1A were smaller than those against casein kinase 1δ and casein kinase 1ε. As with casein kinase 1δ, this DYRK1A has been known as a candidate kinase for phosphorylating tau proteins, and also as a kinase for controlling circadian rhythm. Since the present compounds inhibit the enzyme activity of each of casein kinase 1δ, casein kinase 1ε and DYRK1A, they can be effective therapeutic agents for treating, circadian rhythm disorder and neurodegenerative disease.

2. Concerning Effectiveness of the Compound of the Present Invention

The effectiveness of the casein kinase 1δ and casein kinase 1ε inhibiting compounds for the treatment of circadian rhythm disorder can be proved using the following animal models. Specifically, rats were acclimatized for one or more weeks under light/dark (LD) conditions consisting of a light period for 12 hours and a dark period for 12 hours. Immediately before the beginning of the dark period, the compound represented by the formula (11) was mixed with a solubilizing agent, and the mixture was intraperitoneally administered to each rat at a dose of 60 mg/kg. Immediately after the administration, a statistically significant reduction in momentum and an increase in non-REM sleep amount were observed in the rats to which the compound of the formula (11) was administered, when compared with rats untreated with the compound. On the other hand, with regard to a compound in which as halogen group or the like had not been introduced into the thiophene ring of the compound represented by the formula (2) ((4-((6-methoxy-3-pyridinyl)methylene)-2-(2-thienyl)-5(4H)-oxazolone)), the same test as described above was carried out. As a result, a significant reduction in momentum and an increase in non-REM sleep amount were observed in the rats to which this compound was administered. However, the medicinal effect of the compound of the formula (11) was significantly higher than that of the aforementioned compound in which a halogen group or the like had not been introduced into the thiophene ring ((4-((6-methoxy-3-pyridinyl)methylene)-2-((2-thienyl)-5(4H)-oxazolone)). These results demonstrate that the compound of the formula (11) is effective for the treatment of circadian rhythm disorder.

The activity of the present compound to inhibit casein kinase 1δ having tau as a substrate can be examined using human recombinant casein kinase 1δ (Carna Biosciences; Cat No. 03-103) as an enzyme source and also using human recombinant tau (Sigma-Aldrich; Cat No. T0576) as a phosphorylation substrate. The composition (final concentration) applied during the inhibitory activity measurement assay is as follows.

25 μg/ml casein kinase 1δ, 10 μg/ml tau, the present compound (25 μM to 1 μM), 200 μM ATP, 50 mM HEPES (pH7.4), 10 mM MgCl$_2$, 0.01% Brij-35, 200 μM Na$_3$VO$_4$, and 0.25% DMSO The present compound has previously been allowed to react with the enzyme at room temperature for 15 minutes, and tau is then added to the reaction product. Thereafter, a phosphorylation reaction is carried out for 2 hours. After completion of the phosphorylation reaction, the reaction solution is subjected to Western blotting, so that the phosphorylation of the human recombinant tau transcribed on a PVDF membrane is detected using Phos-tag (NARD Institute, Ltd.; Cat No. BTL-104) according to a chemiluminescence method (ECL Plus; GE Healthcare; Cat No. RPN2132). The PVDF membrane after detection of the phosphorylation reaction is deprobed in accordance with the protocols of the Phos-tag, and thereafter, a total tau protein content can be detected by an antibody reaction.

The membrane is allowed to react with an anti-tau antibody (DAKO Cytomation; Cat No. A0024) used as a primary antibody., and it is then allowed to react with an IR Dye 6801LT-labeled at anti-rabbit secondary antibody (LI-COR; Cat No. 926-68021). Then, infrared fluorescence is detected, and it is used as a signal of total tau protein.

Typhoon (Amersham Biosciences; model 9400) and Odyssey (LI-COR; model 9120) are used, respectively, for detection of the phosphorylation reaction according to chemiluminescence and for detection of a total tau protein according to infrared fluorescence. The ratio of the signal strength of the phosphorylated tau to the signal strength of the total tau protein is obtained, and the obtained ratio is defined as the phosphorylation rate of tau.

The phosphorylation rate of tau in a reaction solution containing the present compound was compared with that in a reaction solution that did not contain the present compound. As a result, significant inhibition against the phosphorylation of the substrate could be observed in reaction solutions containing either the compound of the formula (2) or the compound of the formula (11). These results demonstrate that the compounds of the formulae (2) and (11) are likely to inhibit abnormally excessive tau phosphorylation in central neurodegenerative diseases (e.g. Alzheimer's disease).

The effectiveness of the casein kinase 1δ and casein kinase 1ε inhibiting compounds for central neurodegenerative diseases can be proved using the following animal models. That is, transgenic mice, which excessively express a mutant tau protein causing neurofibrillary degeneration in their brain, are used, and the mice are administered with the inhibitory compound that has been mixed into feed or drinking water for a long period of time. The effectiveness of the inhibitory compound can be proved by pathologically confirming that the degree of causing a loss of synapses and neurological deficit in the administration group is decreased in compared with a non-administration group.

The effectiveness of the casein kinase 1δ and casein kinase 1ε inhibiting compounds for pancreatic cancer can be proved using the following animal models. That is, a human pancreatic cancer cell line (approximately 5,000,000 cells) is cultured in vitro, and the culture is then subcutaneously injected into the dorsal surface of SCID mice. From fourteen days after the injection, the inhibitory compound is mixed with a solubilizing agent (carboxymethyl cellulose, etc.), and the mice are administered with the thus obtained mixture via an oral or intraperitoneal administration. The size of a tumor in the subcutis is observed over time. Moreover, on the 10$^{th}$ day after the administration, the tumor is excised from the subcutis, and the weight thereof is measured, so that the effectiveness of the inhibitor can be proved.

INDUSTRIAL APPLICABILITY

The inhibitor of casein kinase 1δ and casein kinase 1ε of the present invention and the pharmaceutical agent of the present invention comprising the above-described inhibitor as an active ingredient greatly contribute to the development of a pharmaceutical agent useful for the treatment and/or prevention of diseases, with the pathological conditions of which the activation of the casein kinase 1δ or casein kinase 1ε is associated. In particular, the present inhibitor of casein kinase 1δ and casein kinase 1ε and the present pharmaceutical agent greatly contribute to the development of a pharmaceutical agent useful for the treatment and/or prevention of circadian rhythm disorder (including sleep disorder), central neurodegenerative disease and cancer.

The invention claimed is:

1. An oxazolone derivative represented by the following general formula (1):

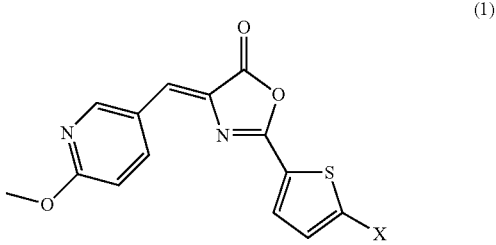

wherein X represents a halogen atom, the halogen atom being any one of a fluorine atom, a chlorine atom, a bromine atom and an iodine atom.

2. A pharmaceutical composition, comprising:
as an active ingredient, the oxazolone derivative according to claim 1, a salt thereof, a solvate thereof, or a hydrate thereof.

* * * * *